United States Patent
LaPointe (10) Patent No.: US 6,752,001 B1
(45) Date of Patent: Jun. 22, 2004

(54) LUBRICANT TESTER

(76) Inventor: Lou LaPointe, 16530 29$^{th}$ Ave. N., Plymouth, MN (US) 55447-1817

( * ) Notice: Subject to any disclaimer, the term of this patent is extended or adjusted under 35 U.S.C. 154(b) by 0 days.

(21) Appl. No.: 10/289,801

(22) Filed: Nov. 7, 2002

(51) Int. Cl.$^7$ .......................... G01N 19/02; G01N 33/26
(52) U.S. Cl. .......................... 73/10; 73/53.05; 73/53.06
(58) Field of Search ....................... 73/10, 53.05, 53.06

(56) References Cited

U.S. PATENT DOCUMENTS

| | | | | |
|---|---|---|---|---|
| 154,922 A | * | 9/1874 | Stapfer ........................... | 73/10 |
| 1,622,481 A | * | 3/1927 | Annis ............................ | 73/10 |
| 2,019,948 A | * | 11/1935 | Beorlage ....................... | 73/10 |
| 2,132,347 A | * | 10/1938 | Anderson ...................... | 73/10 |
| 3,178,928 A | * | 4/1965 | Howe ............................ | 73/9 |
| 3,913,377 A | * | 10/1975 | Lindeman ..................... | 73/10 |
| 4,267,722 A | * | 5/1981 | Hendry ......................... | 73/10 |
| 5,315,860 A | * | 5/1994 | Dreilich et al. ................. | 73/9 |
| 6,145,370 A | * | 11/2000 | Evans ............................ | 73/7 |

* cited by examiner

Primary Examiner—Edward Lefkowitz
Assistant Examiner—Michael Cygan
(74) Attorney, Agent, or Firm—D L Tschida (57) ABSTRACT

An assembly that provides for the mounting of paired sets of lubricant sample holders into balanced, opposed contact with a rotating rotor and whereby comparative data pertaining to measured load, speed and elicited thermal, audio and visual responses are obtained. The coded data is stored for digital comparison. In one assembly, a metal disc is mounted to rotate from a motor drive shaft in a cylinder block and in contact with calibrated sample support bushings biased to contact upper and lower surfaces of the disc. In another construction, an annular cylinder block supports several radially directed, opposed pairs of sample support bushings in biased, tangential contact with a circumferential wall of a cylindrical race or spherical rotor. Pneumatic or hydraulic pressure may be used to augment or load each bushing. In yet another construction, an annular cylinder block supports a pair of opposed weighted lever arms and sample support bushings in tangential contact with a rotor surface. A turnbuckle assembly coupled to the weights permits an adjustment of the center of gravity position of the weights.

29 Claims, 6 Drawing Sheets

LUBRICANT TESTER

BACKGROUND OF THE INVENTION

The present invention relates to lubricant testers and, in particular, to a portable friction tester having balanced, opposed test bushings that are biased with springs, levers and/or pressure to load a rotating rotor (e.g. race, disc or sphere) and wherefrom numerous variables (e.g. torque, angular speed, audio and temperature outputs) are monitored to test the relative lubricating properties of lubricants (e.g. commercial oils and greases).

Classical friction is the resistance to relative motion between two surfaces as a consequence of slip-sticking, plastic deformation and/or welding that occurs with the ultimate generation of heat. Friction can be measured quantitatively and/or qualitatively by visual examination of tested samples. In physics, friction is an energy process that converts the ordered motion of some object into disordered motion and heat.

An important engineering concept in the study of friction and lubrication is the "lubrication parameter" (LP). The lubrication parameter considers friction and lubricity in relation to three factors: sliding speed, load and viscosity of a lubricant sample. The relative control of these three factors determines not only the degree of friction for a specific sample but also wear. Depending upon the physical parameters that indicate friction for a particular test, quantitative measures can be obtained in various units, depending upon the physical property that is monitored and measured.

Wear between two mating surfaces experiencing friction can also elicit a qualitative measure of friction. The degree of wear is found by visual examination of the two mating surfaces after a test. Wear can also be determined, for example, by methods such as particle count analysis and/or magnetic or chemical examination of debris left in a lubricant sample after a test. However, the detection of wear from friction is not a primary goal of this invention because friction analysis and wear analysis are highly dissimilar and not comparable disciplines. For example precise wear analysis would take much longer times of operation and greater PSI loading than this invention is designed for.

Tribology is the study of lubrication and lubricants and their related coefficients of friction, viscosity and lubricity, among other relevant physical properties and parameters. A variety of testers have been developed to test the lubrication properties of all types of lubricants and materials in their various states (i.e. liquid, solid and gas) from grease to oil to plastics, to name a few lubricants. The knowledge of these properties and pertinent wear characteristics allows for the design of improved machines.

Some examples of devices used to test rubber are shown at U.S. Pat. Nos. 6,167,745; 6,334,358 and 6,349,587. Some lubrication/friction testing assemblies are shown at U.S. Pat. Nos. 5,388,442; 5,932,790; 6,145,370 and 6,167,745. Some oil testing assemblies are shown at U.S. Pat. Nos. 3,990,960 and 6,365,413. A force and position related test system for tribological materials is shown at U.S. Pat. No. 5,679,883 and a strain measuring tribological test assembly is shown at U.S. Pat. No. 6,363,798.

The present improved tester was developed to provide a portable, yet accurate lubricant tester that employs an electric or hydraulic motor to drive a rotating surface or rotor (e.g. a disc, race or sphere) at a stable and measured but not necessarily constant speed. At least one pair of sample holders (e.g. bushings) are maintained with a controlled bias to present a constant, known load with the rotating surface in the presence of a lubricant sample (e.g. oil, grease or solid film). The specific loading is measured in pounds force or pressure in pounds per square inch (PSI) and can be adjusted with different combinations of bushings and/or bias springs and/or weighted levers and/or pneumatic/hydraulic pressure to direct the bushings into contact with the rotating surface.

The motor runs briefly for several seconds as two lubricated metal surfaces (e.g. steel or aluminum or copper or iron) are pressed against each other. A loss of RPM, heat, noise and the consumption of power at the motor reflect the resultant drag. The latter outputs can be measured in terms of shaft torque, temperature degrees, RPM, decibels and frequency of noise, hydraulic PSI, amperage draw or voltage drain, among other values. The observed/measured values do not directly yield a calculated coefficient of friction for each oil sample. The values however reflect numbers that can be compared to other samples to provide a relative comparison and give a history. The measured results can also be captured on video or film and/or be analyzed by computer.

SUMMARY OF THE INVENTION

It is a primary object of the invention to provide a portable lubricant tester that supports at least two sample lubricant holders into balanced, opposing contact with a moving surface.

It is further object of the invention to provide a lubricant tester wherein bushings soaked in a sample lubricant and containing a wick soaked in the lubricant or lined with a solid film sample are biased under a known force in opposed resistance to a rotor (e.g. rotating disc, race or spheroid).

It is further object of the invention to provide a generic motor, either electric or hydraulic, typically about one horsepower to drive the rotor to overcome the opposed loading applied by paired sets of sample support bushings.

It is a further object of the invention to provide sample holders or "cylinder blocks" having multiple bores that are symmetrically arranged toward a rotating disc, race or ball rotor and that each contain sample support bushings and resilient biasing members for directing the bushings into contact with the disc, race or ball rotor.

It is further object of the invention to provide a cylinder block having bores that define upper and lower cylinders relative to an intermediate cavity within which a disc rotates and wherein the upper and lower cylinders contain sample supporting bushings and springs to bias the bushings into orthogonal contact with the rotating disc.

It is further object of the invention to resiliently bias each bushing with one or more springs having calibrated spring constants.

It is further object of the invention to resiliently bias each bushing with weighted lever arms.

It is further object of the invention to resiliently bias each bushing with a controlled pneumatic or hydraulic pressure.

It is further object of the invention to provide one or more cylinder blocks having radially directed bores that contain sample supporting bushings biased with springs, weighted levers or fluid pressure to direct the bushings into tangential contact and load a rotating rotor.

The foregoing objects, advantages and distinctions of the invention are obtained in three presently preferred test assemblies. In one preferred construction, the assembly provides an electric motor secured to a rigid base plate. A metal disc is mounted to rotate from the motor drive shaft.

Mounted to the base plate are one or more symmetrically positioned cylinder blocks. Each cylinder block provides a horizontal raceway cavity that partially encompasses the disc and at least one orthogonal bore that defines first and second cylinders. The cylinders each contain appropriate test or sample support bushings lubricated with a test lubricant and one or more calibrated springs or other means that bias the bushings into contact with opposite surfaces of the disc at a known, constant force.

In another construction, a metal race or cylindrical or spherical rotor of substantial thickness is mounted to rotate on the motor drive shaft. Mounted to the base plate are one or more symmetrically positioned cylinder blocks. Each cylinder block provides a number of radially directed bores that define sample support cylinders and which cylinders are aligned in radially opposed relation to each other relative to the drive shaft and rotor. Each cylinder contains a sample support bushing and one or more calibrated springs, weighted levers or other pressurized means bias the bushing into contact with the rotor at a known, constant force.

In another construction, a metal race or spheroid rotor is mounted to rotate on the motor drive shaft. Concentrically mounted to the rotor at a supporting base plate is an annular cylinder block. The cylinder block provides several paired sets of bores that define sample support cylinders and which cylinders are aligned in radially opposed relation to each other relative to the drive shaft and rotor. Each cylinder contains a sample support bushing. Each bushing is biased to contact the rotor via a lever that pivots on an axle secured to the cylinder block. Each lever supports a calibrated weight and whereby a force multiplication (e.g. 2× to 12×) is achieved and a known, constant load force is obtained at the rotor. The levers and weights provide identical, balanced, opposing loading forces, which generate relatively extreme frictional pressures between the bushings. The loading can be augmented or alternatively achieved with a controlled pneumatic or hydraulic pressure. As in all the embodiments, the opposed mountings of the bushings cancels extraneous conditions that may exist, other that the load forces Still other objects, advantages, distinctions and constructions of the invention will become more apparent from the following description with respect to the appended drawings. Similar components and assemblies are referred to in the various drawings with similar alphanumeric reference characters. The description should not be literally construed in limitation of the invention. Rather, the invention should be interpreted within the broad scope of the further appended claims.

Similar structure throughout the drawings is referred to with the same alphanumeric reference numerals and/or characters.

DESCRIPTION OF THE PREFERRED EMBODIMENTS

Figure 1:
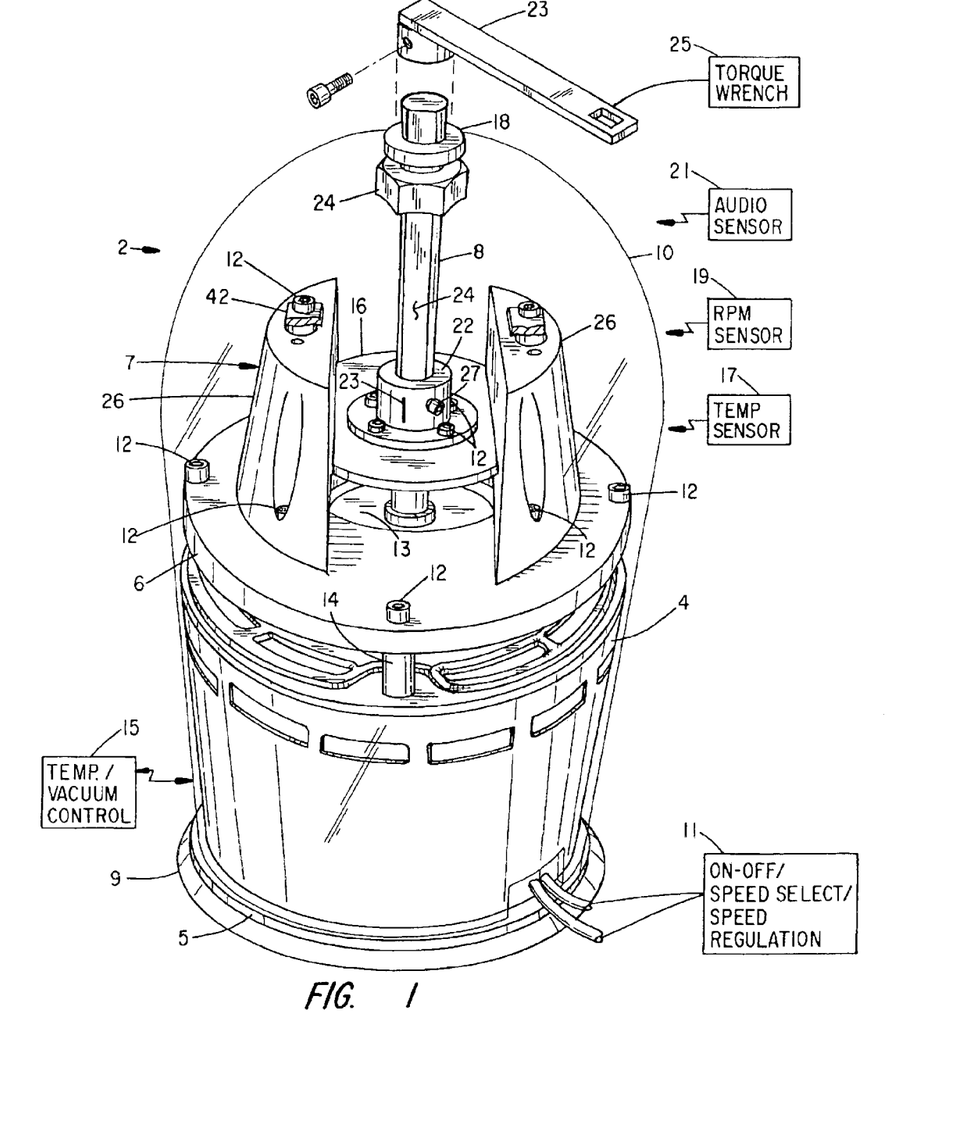
FIG. 1 is a perspective drawing showing one construction of the tester as it appears when assembled during a test, wherein a pair of cylinder blocks support sets of sample bushings above and below a horizontal disc rotor and wherein the tester is covered with a full dome.

Referring to FIG. 1, a perspective drawing is shown in partial exploded assembly to a portable lubricant test assembly 2 of the invention. The assembly 2 includes a motor 4 and securely mounted to which is a base plate 6. A drive shaft 8 of suitable length extends through the base plate 6 and through an overlying clear dome or cover 10 that mounts onto a lip or flange 5 of a support plate 9.

The configuration or arrangement 7 of the test assembly 2 as depicted at FIG. 1 is organized to preferably test light oil or motor oil lubricants and operates at relatively low-speeds on the order of 500 to 1000 revolutions per minute (RPM). A nominal speed of 1075 RPM is typically used for light oil lubricants. A suitable speed controller 11 is coupled to the motor 4 and provides "on/off" control, speed selection and speed regulation at each selected speed to accommodate each test lubricant. Suitable speed and torque characteristics can be obtained with a motor 4 sized from $1/8$ to 1 hp. A hydraulic motor 4 might also be used that employs a suitable hydraulic pump and hydraulic control system.

The clear plastic cover 10 is supported to the support plate 9 to contain lubricant and debris that might splash or be thrown about during testing. A "sling" seal 13 is typically provided below the base plate 6 to prevent oil from draining into the motor 4; although in some other arrangements of the tester 2, the motor 4 could be horizontally mounted thus making a sling seal 13 unnecessary.

The internal temperature of the tester 2 is normally held at room temperature, but the cover 10 may also be supplied with heated or cooled air via suitable accessory temperature and vacuum control equipment 15 to control the internal atmosphere of the tester assembly 2 within a range such as 0 to 300° F. The latter range encompasses the typical measurement temperatures for viscosity tests (i.e. 0, 100 and 212° F.).

The space beneath the cover 10 may also be subjected to a vacuum. In such instances, the test space can be coupled to the accessory equipment 15 via couplings through the support plate 9 or through the walls of the cover 10. Whatever environment is employed inside the cover 10, the environment should be consistent across all lubricant samples tested.

The clear walls of the cover 10 also facilitate visual monitoring and/or the video taping of each test. Accessory sensing equipment can be directed relative to the cover 10 to monitor each test. That is, temperature-sensing equipment 17 (e.g. a laser temperature sensor) measures the heat buildup due to the friction allowed by an oil sample. An RPM sensor 19 (e.g. a laser tachometer) monitors the speed of rotation of the drive shaft 8 and the rotor components attached to the shaft 8 via an indicia mark 23 at a coupler 22. Audio sensing equipment 21 (e.g. an audio decibel detector) can simultaneously measure noise that emanates from the assembly 2 and that arise from frictional heat and molecular vibrations and radiation at the contact area of sample support bushings 20 with a rotor for example a rotating disc 16, discussed below. The audio sensor 21 is typically mounted either to the cover 10 or within 6 inches of the cover 10.

The base plate 6 is supported to the motor 4 with a number of fasteners 12 and standoffs 14. The standoffs 14 allow free circulation of air over the motor 4 and facilitate the positioning of the oil seal 13 or the routing of any necessary conductors fitted to sensors, heaters, pressure lines and/or vacuum lines or other accessory support equipment through the support plate 9 and/or base plate 6. The standoffs 14 also accommodate any vibrations that may emanate from the assembly 2 and any shimming that is necessary to assure that the base plate 6 is supported substantially orthogonal to the drive shaft 8.

For the full dome cover 10, the length of the drive shaft 8 is selected to mount through a bearing or bronze bushing 18 at the top of the cover 10. A shorter shaft 8 can be used with a hemispherical, half-dome cover 48 or 71 that are shown and discussed below with respect to other arrangements of the test assembly 2. The bearing 18 assists in stabilizing the rotation of the shaft 8 and centering the shaft 8 relative to the rotating disc rotor 16 and sample support bushings 20. An extension piece is generally not required with the shaft 8 and care is exerted to assure that any forces on the shaft 8 are balanced to avoid any condition that might damage the shaft 8 and/or create unwanted oscillations.

Before covering the assembly 2, a wrench adapter 23 is typically secured to the top of the shaft 8 and a torque wrench 25 of suitable size is fitted to the adapter 23 to measure the static torque and load on the disc rotor 16 and motor 4, before starting the motor 4. The torque wrench 25 is particularly used to rotate the exposed end of the shaft 8 and measure the initial mechanical load that is presented to the motor 4 by a number of lubricated sample support bushings 20 shown at FIGS. 3 and 4 biased into contact with the disc 16.

Figure 2:
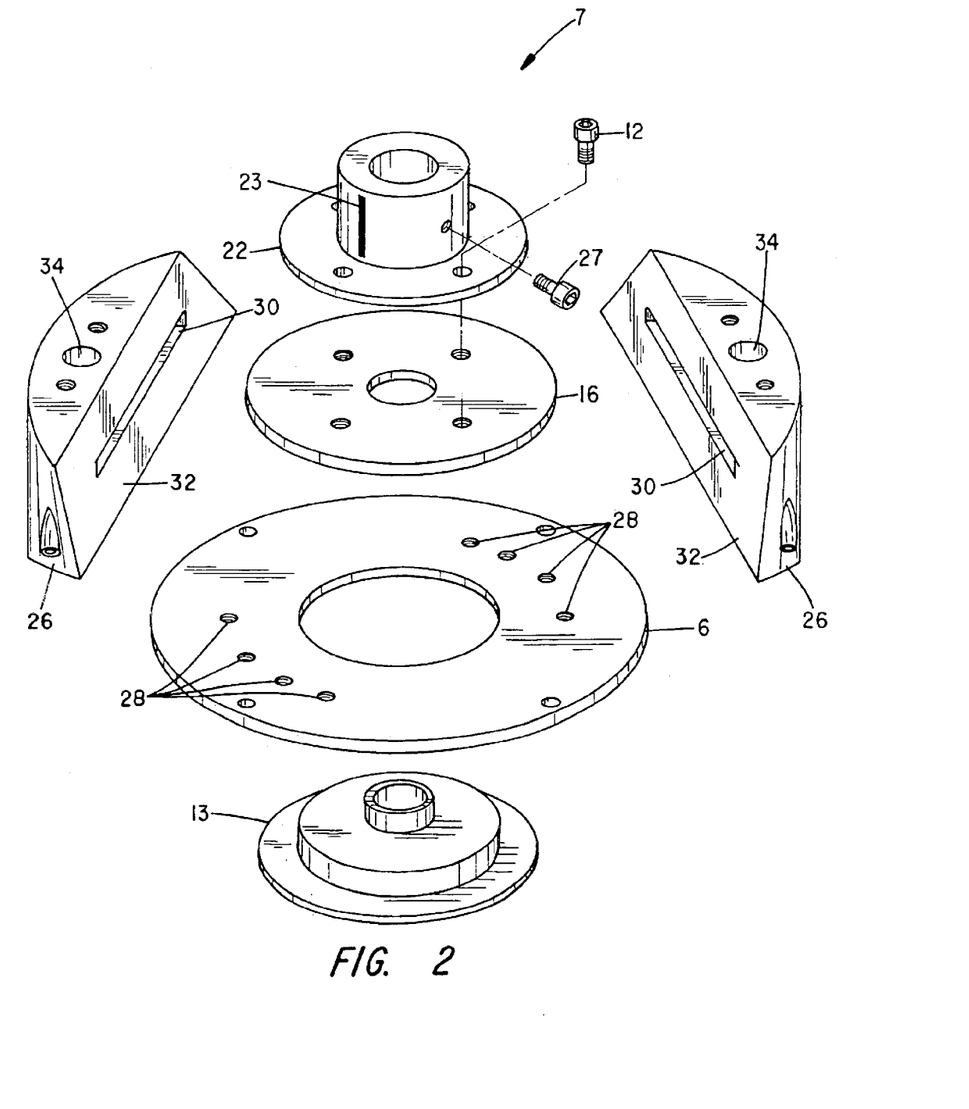
FIG. 2 is a perspective drawing shown in exploded assembly to the base plate, disc coupler and supporting cylinder blocks of FIG. 1.

A disc type rotor 16 is separately secured to the drive shaft 8 with a number of fasteners 12 and the disc coupler 22 shown in FIG. 2. The coupler 22 is secured to the shaft 8 at a flat spot or other suitably shaped surfaces 24 with one or more setscrew fasteners 27. The coupler 22 assures that the plane of the disc 16 lies parallel to the base plate 6 and orthogonal to the shaft 8 and is aligned with the cylinder block(s) 26 that contain the sample support bushings.

The disc 16 is constructed of steel that is suitably hardened to a hardness rating on the order of 55 to 60 Rockwell on the "C" scale to withstand abrasion and the forces of the paired sets of sample support bushings 20 supported in contact with the disc 16. The disc 16 exhibits a nominal 3-inch diameter and a thickness of 0.1-inch, which is sufficient for testing motor oils and light gear oils. The hardness and size of the disc 16 can be varied as necessary to accommodate other tested lubricants.

Figure 3:
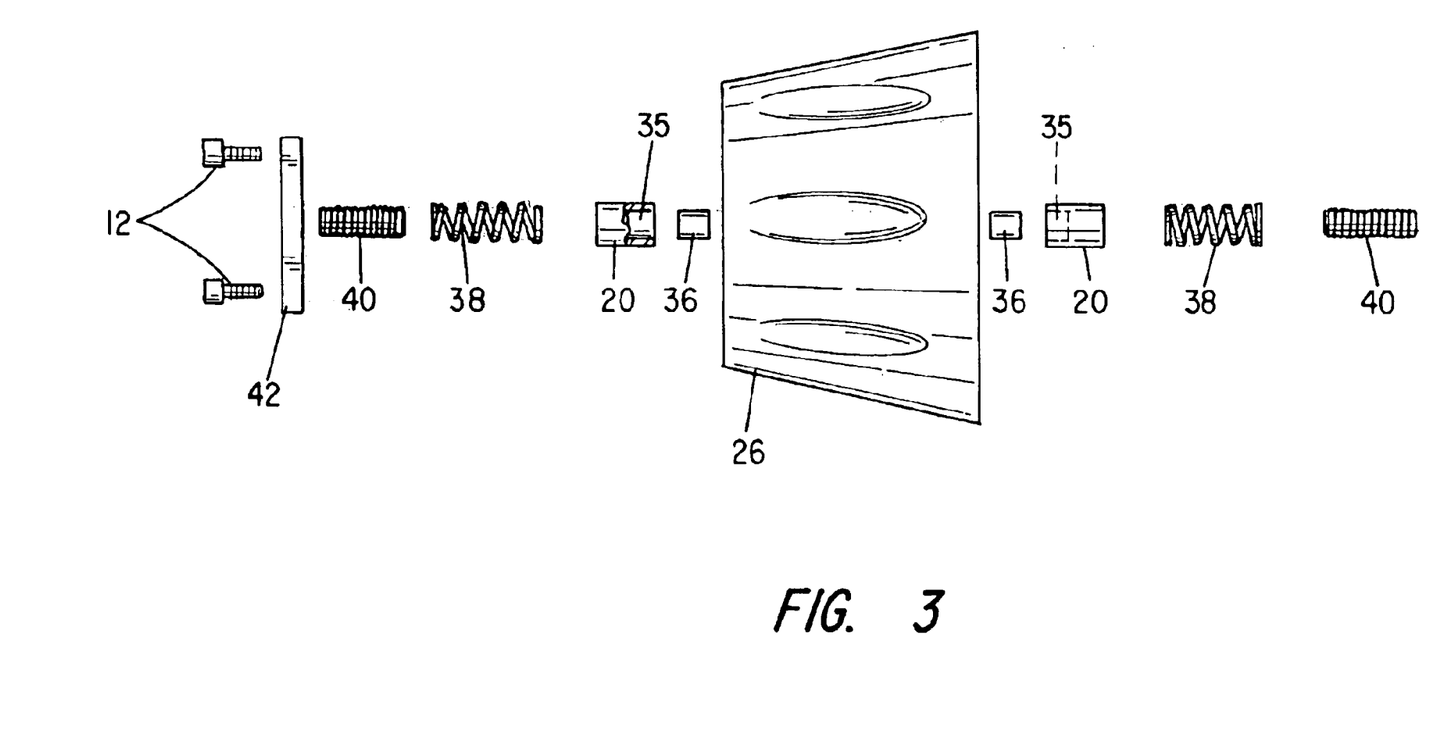
FIG. 3 is a perspective drawing shown in exploded assembly to one of the cylinder blocks and a typically contained set of sample support bushings, lubricant soaked wicks, bias springs and retainer.

With additional attention to FIGS. 2 and 3, mounted to the base plate 6 in opposing relation to each other is a pair of cylinder blocks 26. The cylinder blocks 26 are secured to the base plate 6 with fasteners 12 that extend through the sides of the blocks 26 and fasten to threaded holes 28 in the base plate 6.

A slot or disc cavity 30 is formed into a sidewall 32 of each cylinder block 26 and is shaped and sized to allow for the free rotation of the disc 16 within the cavity 30. The cavity 30 incidentally acts as an oil reservoir to capture and supply excess oil to the contact area between the spinning disc 16 and sample support bushings 20 in contact therewith.

A bore 34 extends through each block 26 orthogonal to the cavity 30. The bore 34 defines upper and lower cylinders relative to the disc 16. Two sample holders or sample support bushings 20 are contained in the bore 34 to separately contact the upper and lower surfaces of the disc 16.

FIG. 3 depicts one of the cylinder blocks 26 in exploded assembly relative to hollow sample support bushing 20. Depending upon the lubricants to be tested, the area of contact and desired loading, the bushing 20 can be either solid or hollow. A hollow bushing 20 provides greater loading. The bushings 20 can be constructed of steel, bronze, iron, aluminum or plastic, among other materials. Although cylindrical bushings 20 are preferred, the shape of the side and end walls of the bushings 20 and mating bores 34 can be varied (e.g. square, rectangular, rounded, elliptical etc.)

The bushings 20 used for testing light lubricants are presently constructed with a hollow end cavity 35 that is sized to contain a cloth fabric wick 36. The cavity may extend partially or completely through the bushing 20. The wick 36 is normally soaked with the test lubricant. The wick 36 thus acts as a reservoir and assures an adequate, but not excessive film of lubricant, is maintained at the contact surface between the bushing 20 with the disc 16 over the period of the test, which is typically 5 to 60 seconds or until lubrication failure is indicated.

Figure 5:
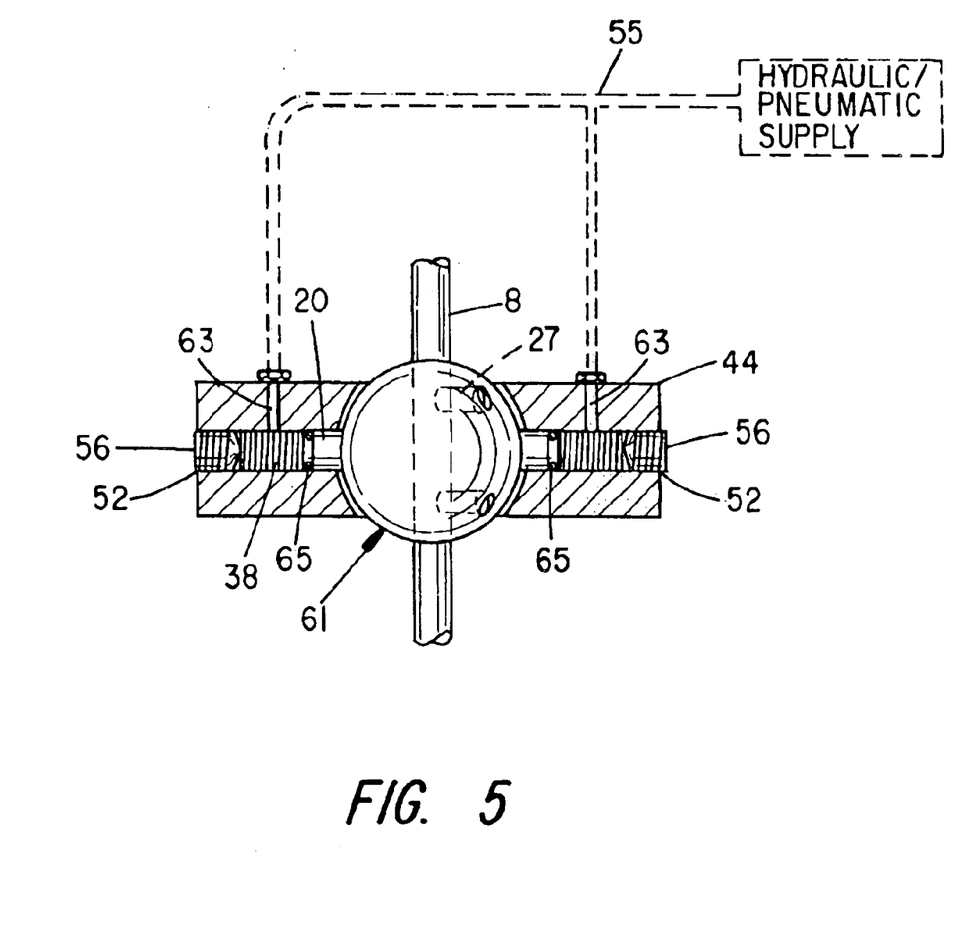
FIG. 5 is a cross section view to a spherical rotor aligned with an annular cylinder block and two tangentially supported, resiliently biased sample support bushings.

The presence of a suitable lubricant film is assured by soaking the bushings 20, disc 16 (race 57 or ball rotor 61), along with the wick pieces 36, with the test lubricant prior to assembling the tester 2. The bushings 20 are almost never installed dry. If a solid film material is being tested, a solid bushing 20 can be used with the material coated to the bushing 20 and/or on the disc 16 so friction contact occurs between the coated surfaces.

The bushings 20 may also be coated or plated with gold, lead or other suitable material compatible with the testing of a particular lubricant and/or special surface. The ends of the bushings 20 are normally ground flat or square with their length but may be ground with a crown or radius or ball shaped ends, if desired. The end surfaces of the bushings 20 may further be treated to alter the friction characteristics during testing. The working surface finish of the bushings is selected to be in a range around 16-microinch RMS, unless otherwise required. An excessive polish of under an 8-microinch RMS surface finish may create too much friction. Surface treatments might consist of polishing, glass beading, sand blasting or abrasive tumbling to alter surface friction.

Each bushing 20 is typically, resiliently supported within the cylinder block 26 with a single outer spring 38. As necessary, an inner spring 40 is used in instances where stiff springs and strong tension are required. In this event the diameter of the spring 40 is sized to mount in concentric, coaxial relation to the spring 38. An equal number of springs 38 of identical spring constants are mounted to support each bushing 20. The springs 38 abut the bushings 20 at one end and the base plate 6 at the bottom of the cylinder block 26 and a spring retainer 42 secured to the top of the cylinder block 26 with fasteners 12.

The springs 38 are right hand (RH) wound to a preferred diameter (e.g. ⅜-inch) and are presently constructed from a number of different wire diameters to offer spring constants of a suitable range to accommodate different test requirements. The springs 38 are presently sized to accommodate forces of 5 to 30 pounds per spring. A variety of different loading conditions can thereby be obtained. The smaller diameter, left hand (LH) wound spring 40, approximately ¼-inch diameter, expands the range of available loading forces. The inner spring 40 may produce forces of 15 to 30 pounds per spring.

Although springs 38 and 40 are presently used, other resilient materials that exhibit desired loading forces might be substituted (e.g. plastics, nylons, elastomers or impregnated materials etc.). Other biasing mechanisms may also be included, such as in the fashion of the lever assembly discussed with respect to FIG. 6 to obtain increased contact forces between any rotor and the bushings 20. In some cases, controlled hydraulic or pneumatic pressure (e.g. in the range of 20 to 300 PSI) may be introduced into a cylinder block via included ports and paths to exert increased loading forces against the bushings 20 than are achievable with the springs 38 and/or 40.

A suitable number of cylinder blocks 26 are assembled for each test with an appropriate spring configuration. The numbers of cylinder blocks 26 and bushings 20 used depends upon the type of lubricant to be tested and necessary PSI loading requirement. The specific PSI load is the aggregate of the total spring force divided by the cumulative area of bushing contact.

Each bushing 20 carries an ID number and the bushings 20 are typically never re-used, nor are any lubricant samples. The bushings 20 have two usable ends and may be flipped to expose the virgin end to permit use for two tests. All bushings 20 are saved and recorded, even in the instance of an aborted test. The physical wear to a solid bushing should be negligible with a good lubricant. New bushings 20 or a virgin end are generally always employed for every test.

Figure 4:
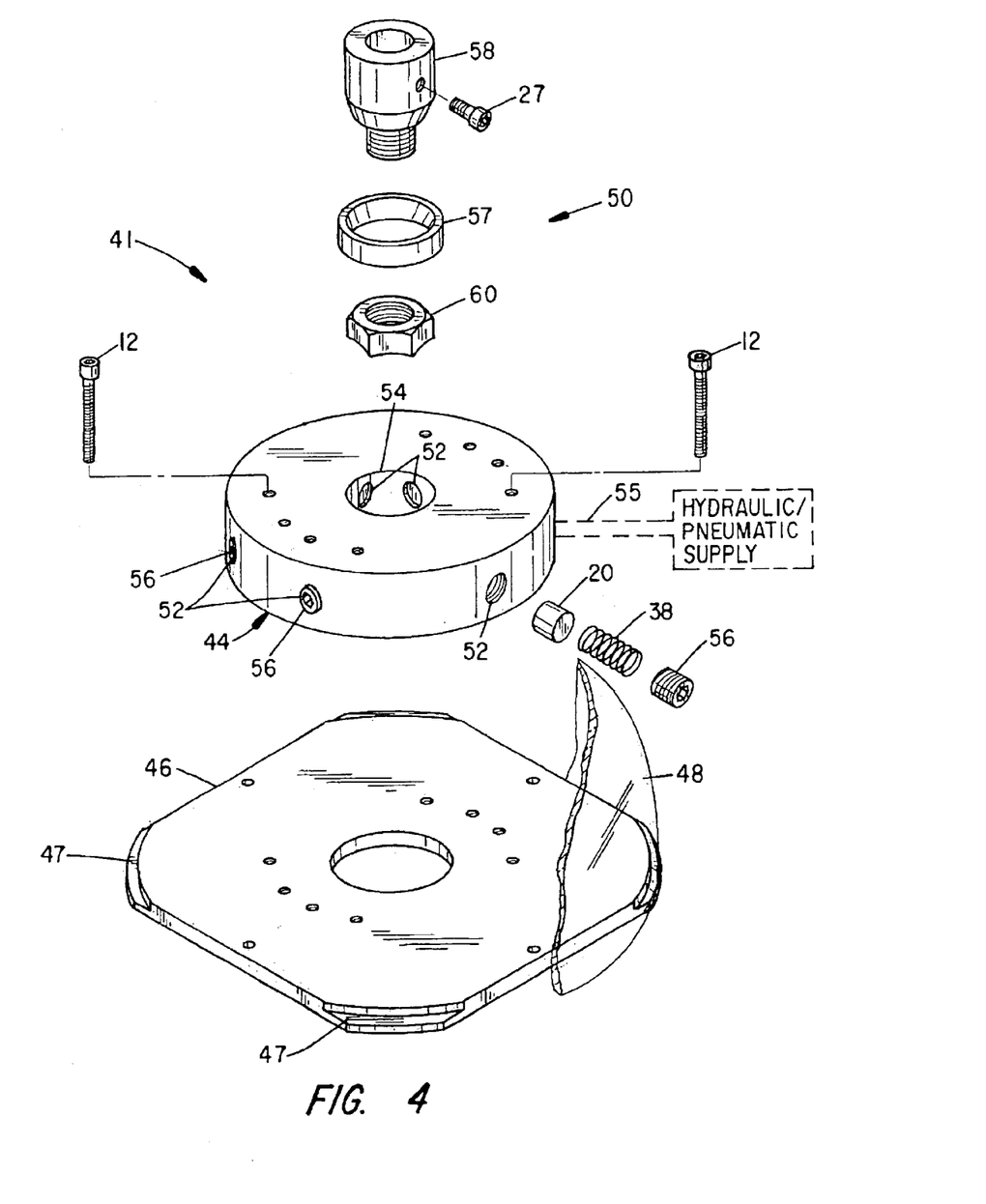
FIG. 4 is a perspective drawing shown in exploded assembly to a second arrangement of the tester, wherein a single annular, cylinder block is mounted to a base plate and opposed sets of spring biased (or pressure biased) sample support bushings are tangentially biased against vertical, cylindrical surfaces of a rotor that is concentrically mounted relative to the cylinder block and a hemispherical dome is supported to peripheral corner edges of the base plate.

With attention to FIG. 4, another arrangement 41 of the tester 2 is shown in exploded assembly and partial cutaway and wherein an annular cylinder block 44 is secured to a base plate 46. Corner flanges 47 mate with a hemispherical dome 48. The cylinder block 44 is constructed to support up to three sets of sample support bushings 20 in tangential contact with a cylindrical race or rotor assembly 50 that is concentrically secured to the drive shaft 8.

The horizontal tester arrangement 41 exhibits a relatively low vertical profile in contrast to the tester arrangement 7 of FIG. 1. The arrangement 41 allows for an increased number of bushings 20 and comparatively increased loading at the rotor assembly 50. The arrangement 41 is particularly suited to test gear oils or engine assembly lubricants or general EP greases. The loading can be augmented with controlled hydraulic or pneumatic pressures. The horizontal arrangement 41 uses a single cylinder block 44.

Each bushing 20 is mounted within a partially threaded bore 52 that is radially directed toward the shaft 8. The bores 52 are arranged such that each bushing 20 is symmetrically aligned to a bushing 20 at an opposite surface of a center bore 54 of the cylinder block 44. Extraneous forces such as from tolerance differences, shaft side forces, drag or the like, are thereby cancelled or balanced in a similar fashion to the arrangement 7 of FIG. 1 and do not affect measurements. Other known testers do not employ the foregoing force cancellation and instead exerts a single direction frictional load. Consequently and unintentionally, possible extraneous forces are present in predecessor equipment that can taint the test data of such testers.

One or more springs 38 and/or 40 resiliently bias each bushing 20 into contact with the circumferential edge of the rotor assembly 50. A threaded plug 56 secures each spring 38 and bushing 20 set to each bore 54. The threaded plug 56 also seals each bore 52 in case fluid or air pressure is applied to the cylinder block 44 to enhance the force acting on each bushing 20. In this regard, the block 44 may be adapted to accept one or more conduits 55 (shown in dashed line) to admit a pressurized hydraulic fluid or pneumatic gas via internal paths (not shown) to each of the bores 52. A regulated pressure might thus be applied in substitution or in conjunction with the springs 38 and 40.

The rotor assembly 50 includes a hardened cylindrical walled race 57 that is supported to a tapered coupler 58 with a nut 60. The coupler 58 is secured to the shaft 8 with a setscrew 27 such that the sidewalls or the inner bore 54 are substantially parallel and concentric to the circumferential outer wall of the race 57. The race 57 is approximately 9 mm. wide and is substantially thicker than the disc 16. The thickness or width of the race 57 can be adjusted as desired, provided a sufficient surface is provided to obtain contact with the bushings 20. The race 57 exhibits a typical hardness in the range of 57 to 62 Rockwell on the C scale.

With attention to FIG. 5, a hardened spheroid or ball-shaped rotor 61 is shown that may be substituted for the rotor assembly 50. One or more setscrews 27 secure the spherical rotor 61 to the shaft 8. The spherical rotor 61 might alternatively be secured to the coupler 58 in lieu of the race 57.

The reduced contact surface of the test bushings 20 with the spherical rotor 61 creates relatively higher PSI loading and more severe friction. The race 57 or spherical rotor 61, when used against crowned bushings 20, would typically be used to test high EP lubes such as heavy-duty gear oils.

As with the block 44 of FIG. 4, conduits 55 might also be adapted to couple to internal paths 63 that conduct pressurized hydraulic fluids or pneumatic air under controlled pressure from an outside source into the cylinder bores to augment or substitute for a force presented by springs 38 and/or 40 against the bushings 20. In such instance, O'rings 65 or other seals would normally be adapted to the bores 52 to prevent pressure loss.

Figure 6:
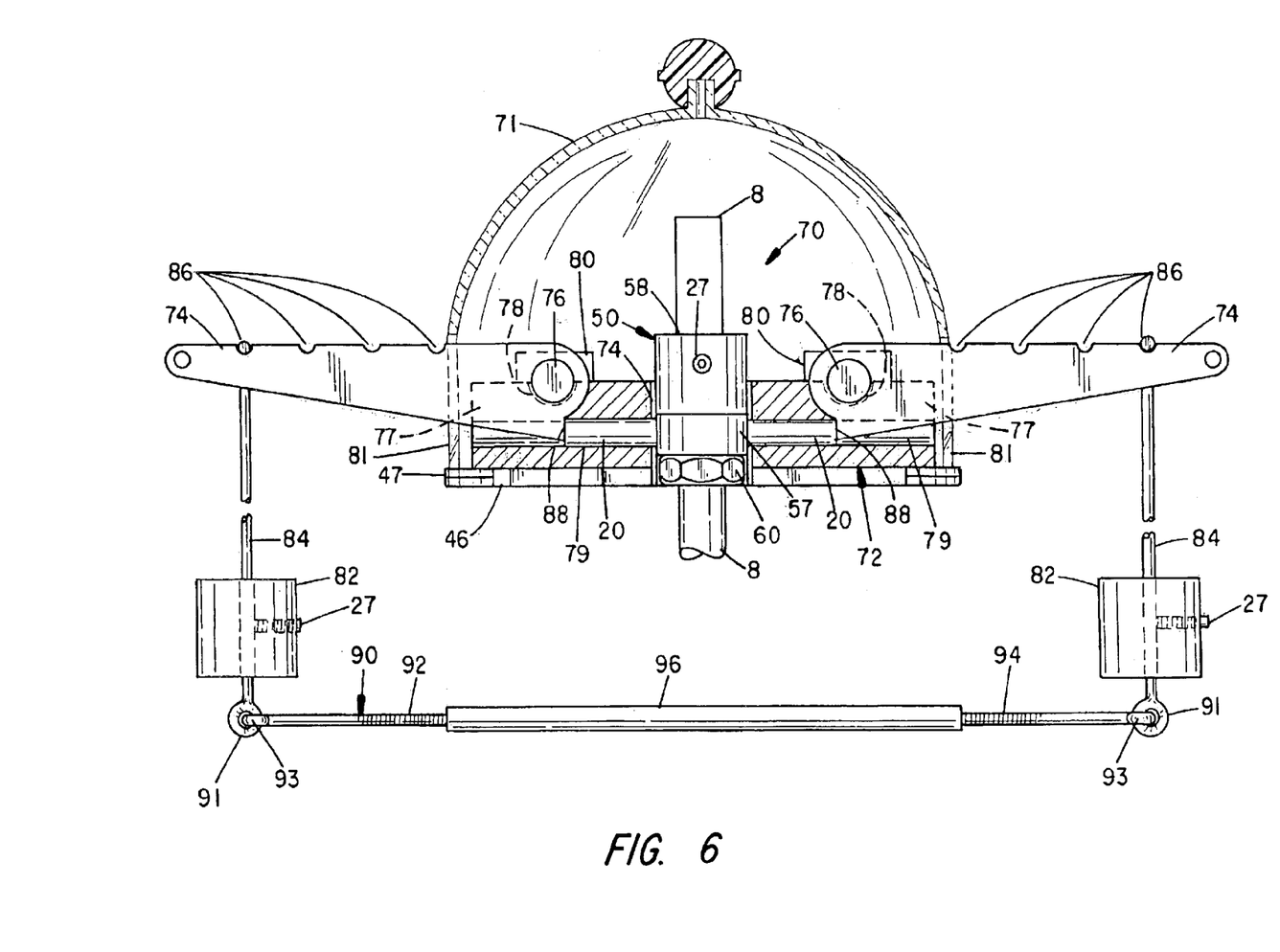
FIG. 6 is a cross section view to a third arrangement of a hemispherical dome covered tester wherein a pair of weight supporting lever arms are mounted to pivot from axles secured to an annular cylinder block and located on a base plate to bias sample support bushings to tangentially contact a concentrically aligned vertical rotor.

FIG. 6 depicts yet another arrangement 70 of the tester 2 that develops increased bushing loads that can test heavy-duty gear oils, greases etc. The arrangement 70 provides a base plate 46 that supports a hemispherical cover 71. An annular cylinder block 72 is secured to the base plate 46. A rotor assembly 50 is concentrically mounted in a bore 74 of the cylinder block 72.

A pair of lever arms 74 are supported 180° from each other with pivot axles 76 that are contained in channels 78 formed into the cylinder block 72. The lever arms 74 pivot within vertical slots 77 in the cylinder block 72 that extend coaxial to and in communication with bores 79 that contain individual test bushings 20. Other pairs of lever arms 74 can be provided, but are not believed to be presently required. Retainers 80, secured with suitable fasteners to the block 72, retain the pivot axles 76 to the cylinder block 72. The lever arms 74 extend through slots 81 in the cover 48.

Identical weights 82 (e.g. 10–50 pounds) are suspended with hangers 84 that can be positioned at several notches 86 along the lever arms 74. Setscrews 27 secure the weights 82 at a desired point along the hangers 84. The number and spacing between the notches 86 can be established as desired and presently span an approximate range between 2 to 6 inches from each pivot axle 76. The position of the weights 82 determines the torque multiplication loading force exerted by the levers 74 on the bushings 20 and against the race 57.

A turnbuckle assembly 90 is secured between the ends of the hangers 84 and permits a controlled, fine adjustment to position the center of gravity provided by the arms 74 and weights 82. The turnbuckle assembly 90 is supported from eyelets 91 at the hangers 84 that receive hooked ends 93 of left and right, length adjustable arms 92 and 94. The arms 92 and 94 provide left and right hand threads and interlock with a threaded center coupler 96. The arms 92 and 94 can be extended and retracted inward or outward relative to the coupler 92 as part of any test to tailor the loading at the rotor 50.

For any test, identical weights 82 are positioned along the arms 74 to provide equal opposed loading forces. The weights 82 particularly induce lever arm surfaces 88 to contact and direct the bushings 20 into contact with the rotor or race 57. Substantially increased bias forces are thereby directed against the bushings 20, versus the tester arrangements 7 and 41. Taken with the relatively small bushing contact area, the loading developed at the rotor assembly 50 is substantially increased. Loads in the range of 100 to several thousand PSI can particularly be developed at the rotor 50.

As noted from each of the foregoing arrangements 7, 41 and 70 of the tester 2, one or more paired sets of two bushings 20 are always mounted in balanced, opposing relation to each other to contact a suitable rotor, for example, disc 16, cylindrical race 57 or spherical ball 61. The vertical arrangement 7 permits the loading of the disc 16 with 4 bushings 20; the horizontal arrangement 41 allows for six bushings 20; and the lever arm arrangement 70 accommodates two bushings 20. Such balanced mountings particularly avoid measurement of any extraneous forces that can arise from the tolerance and operating differences of the electro-mechanical assembly 2, such as the noted bearing wear. The force cancellation feature of the invention also permits the tester 2 to be constructed in lightweight designs that are not as massive as some other commercially available testers.

Precision machining of the tester parts also assures consistent and correct rotation and physical behavior, as consistency is an essential property of the tester 2 as a scientific tool to evaluate oils. Consistency is a desirable feature of this invention so that lubricants can be tested this year and be examined again 10 years from now and get identical results. This goal of standardization and precision is important if not crucial.

As further noted, a variety of lubricants can be tested with controlled, repeatable accuracy with the foregoing arrangements 7, 41 and 70 of the test assembly 2. The tester assembly 2 particularly provides a meaningful collection of data for each test as to measured load, rotational speed, thermal changes, audible sounds, vibrations and visual data and from which comparative judgments can be made between tested lubricants. An exemplary test results data entry sheet is shown below and is filled out as the testing proceeds then is saved and recorded.

Upon digitally coding and storing the collected information and data for each test procedure into a suitable database, such practical comparisons can also be made with relative objectivity and ease. The test assembly 2, however, does not directly yield a coefficient of friction for each sample tested, as do some other simplistic oil testing devices. The reason is that the coefficient of friction is a changing dependent value best described with a differential equation dependent on many factors such as the oil lubricity, viscosity, additive package, surface properties, PSI loading, sliding speed of contact, surface temperature, materials and power. Some of these factors naturally affect the coefficient more than others.

| Test Results Data Sheet | |
| --- | --- |
| Date: | Model Tester: Test No. |
| Total bushings: | Type of Bushings: |
| Start Temperature: | End Temperature: |
| Free RPM 1: | ISO Viscosity: |
| Free RPM 2: | |
| Loaded RPM 1 | |
| Loaded RPM 2: | Average RPM Drop: |
| Starting Decibels 1: | |
| Starting Decibels 2: | |
| Loaded Decibels 1: | |
| Loaded Decibels 2: | Average Decibel Rise: |
| Load on Springs: | Load on Levers: |
| Spring Loading in Pounds: | Duration of Trial: seconds |
| Fluid Pressure if Used: | Time to Failure: seconds |
| Company Name: | Operator Name: |
| Details regarding Disc, Race or Sphere: | |
| Special Results and Database Code: | |
| Comments: | |
| List all Serial Numbers: | |

It should be further recalled that in certain test circumstances it might be deemed necessary to control the temperature at the tester 2 to a temperature environment in the range of 0° F. to 300° F. versus the normal testing temperature of a nominal 70° F. It may also be desired to subject the test space to a vacuum. In such instances, the test space beneath the cover 10 can be coupled to suitable accessory equipment via couplings through the base plate 6 or through holes in the plastic cover 10. Whatever environment is employed inside the cover 10, that environment should be consistent across all lubricant samples of the same type tested in the same range.

While the invention has been described with respect to a number of preferred constructions and considered improvements or alternatives thereto, still other constructions may be suggested to those skilled in the art. It is also to be appreciated that selected ones of the foregoing features, such as the different rotors, cylinder blocks and biasing mechanisms, can be arranged in different combinations or adapted to other testers to provide a variety of improved lubricant testing assemblies. The foregoing description should therefore be construed to include all those embodiments within the spirit and scope of the following claims.

What is claimed is:

1. A lubricant testing assembly comprising:
   a) a motor having a drive shaft;
   b) a rotor mounted to said drive shaft;
   c) a block mounted to said motor and wherein first and second springs are respectively mounted in first and second coaxially opposed bores to bias first and second sample supports lubricated with a test lubricant into contact with said rotor; and
   d) means for measuring an initial load presented by said first and second sample supports on said rotor and for measuring changes in a plurality of test variables upon rotating said rotor, whereby relative comparisons can be made in the data measured from each tested lubricant sample.

2. A lubricant testing assembly as set forth in claim 1 including a base plate mounted to said motor and a cover mounted to said base plate for enclosing said rotor and block.

3. A lubricant testing assembly as set forth in claim 2 wherein a bushing is mounted to said cover and said drive shaft extends through said bushing.

4. A lubricant testing assembly as set forth in claim 1 wherein said measuring means measures changes in test variables selected from a class including temperature changes at said rotor, rotation speed changes at said rotor, audible noise and wear at said sample supports.

5. A lubricant testing assembly as set forth in claim 1 wherein said block comprises a member having a cavity within which a portion of said rotor rotates, wherein said first and second bores are aligned orthogonal to and in communication with said cavity.

6. A lubricant testing assembly as set forth in claim 5 wherein said rotor comprises a disc.

7. A lubricant testing assembly as set forth in claim 1 wherein said first and second sample supports comprise first and second bushings, wherein said first and second bushings each have an exposed hollow cavity, and wherein a wick member lubricated with a sample lubricant is mounted in said cavity and exposed to contact said rotor.

8. A lubricant testing assembly as set forth in claim 1 wherein said first and second bores are aligned in radially opposed relation to one another relative to said drive shaft.

9. A lubricant testing assembly as set forth in claim 1 including a pressurized media and means for coupling said media to said first and second bores to bias said first and second sample supports into contact with said rotor.

10. A lubricant testing assembly as set forth in claim 1 wherein said block means comprises an annular member having a central through bore, wherein said rotor mounts in said through bore and wherein said first and second bores communicate orthogonally with said through bore.

11. A lubricant testing assembly comprising:
a) a motor having a drive shaft;
b) a base plate mounted to said motor;
c) a rotor mounted to said drive shaft;
d) a block mounted to said base plate having a cavity within which a portion of said rotor rotates and having first and second coaxial bores aligned orthogonal to and in communication with said cavity, wherein first and second sample supports lubricated with a test lubricant are mounted in said first and second bores along with first and second resilient members, such that said first and second sample supports are resiliently biased to contact said rotor and wherein said sample supports are mounted in opposed coaxial relation to one another;
e) a cover mounted to said base plate for enclosing said rotor and block means; and
f) means for measuring the load presented by said first and second sample supports on said rotor and for measuring changes in a plurality of test variables upon rotating said rotor, whereby relative comparisons can be made to the data measured from each tested lubricant sample.

12. A lubricant testing assembly as set forth in claim 11 wherein a bushing is mounted to said a cover and said drive shaft extends through said bushing.

13. A lubricant testing assembly as set forth in claim 12 wherein first and second springs are mounted in said first and second bores to resiliently bias said first and second sample supports into contact with said rotor.

14. A lubricant testing assembly comprising:
a) a motor having a drive shaft;
b) a base plate mounted to said motor;
c) a rotor mounted to said drive shaft;
d) first and second sample supports supporting samples of a test lubricant; and
e) an annular block mounted to said base plate and having a through bore wherein said rotor mounts, wherein first and second bores are aligned in orthogonal radially opposed relation to one another relative to said through bore to contact a circumferential surface of said rotor, and wherein said first and second sample supports are mounted in said first and second bores, and including means for biasing said first and second sample supports into contact with said rotor;
f) a cover mounted to said base plate for enclosing said rotor and block; and
g) means for measuring an initial load presented by said first and second sample supports on said rotor and for measuring changes in a plurality of test variables upon rotating said rotor, whereby relative comparisons can be made in the data measured from each tested lubricant sample.

15. A lubricant testing assembly as set forth in claim 14 wherein said first and second sample supports comprise first and second bushings, wherein first and second springs resiliently bias said first and second bushings, wherein said first and second bushings have an exposed hollow cavity, and wherein a wick member lubricated with a sample lubricant is mounted in said cavity of each bushing and exposed to contact said rotor.

16. A lubricant testing assembly as set forth in claim 14 including a pressurized media and means for coupling said media to bias said first and second sample supports into contact with said rotor.

17. A lubricant testing assembly as set forth in claim 14 including first and second levers mounted to pivot relative to said block, wherein first and second weights are coupled to said respective first and second levers and wherein surfaces of said first and second levers bias said first and second sample supports into contact with said rotor.

18. A lubricant testing assembly comprising:
a) a motor having a drive shaft;
b) a rotor mounted to said drive shaft;
c) first and second sample supports supporting samples of a test lubricant; and
d) a block mounted to said motor comprising an annular member having a central through bore, wherein said rotor mounts in said through bore, wherein first and second bores are aligned in orthogonal radially opposed relation to one another relative to said rotor, wherein first and second sample supports are mounted in said first and second bores to contact a circumferential surface of said rotor;
e) first and second lever arms mounted to pivot relative to said block, wherein first and second weights are coupled to said respective first and second lever arms and wherein surfaces of said first and second lever arms bias said first and second sample supports into contact with said rotor;
f) a cover for enclosing said rotor and block; and
g) means for measuring an initial load presented by said first and second sample supports on said rotor and for measuring changes in a plurality of test variables upon rotating said rotor, whereby relative comparisons can be made in the data measured from each tested lubricant sample.

19. A lubricant testing assembly as set forth in claim 18 including means for adjusting the center of gravity of said first and second weights relative to said first and second lever arms.

20. A lubricant testing assembly as set forth in claim 18 including first and second hangers mounted to suspend said first and second weights from said first and second lever arms and wherein said weight adjusting means comprises a length adjustable member coupled to said first and second hangers, whereby an angular orientation between said first and second hangers relative to said first and second lever arms can be varied.

21. A lubricant testing assembly comprising:
   a) a motor having a drive shaft;
   b) a rotor mounted to said drive shaft;
   c) a block mounted to said motor and supporting at least first and second bushings, wherein each of said first and second bushings has an exposed hollow cavity containing a wick member lubricated with a sample lubricant and exposed to contact said rotor, and wherein said first and second bushings are mounted in opposed coaxial relation to one another and in contact with said rotor; and
   d) means for measuring an initial load presented by said first and second bushings on said rotor and for measuring changes in a plurality of test variables upon rotating said rotor, whereby relative comparisons can be made in the data measured from each tested lubricant sample.

22. A lubricant testing assembly as set forth in claim 21 including first and second levers mounted to pivot relative to said block, wherein first and second weights are coupled to said respective first and second levers and wherein surfaces of said first and second levers bias said first and second bushings into contact with said rotor.

23. A lubricant testing assembly as set forth in claim 21 wherein said first and second bushings are resiliently biased into contact with said rotor.

24. A lubricant testing assembly as set forth in claim 23 wherein first and second springs are mounted in said first and second bores to resiliently bias said first and second sample supports into contact with said rotor.

25. A lubricant testing assembly as set forth in claim 21 wherein first and second bores are located in first and second blocks and said first and second bushings are mounted in said first and second bores.

26. A lubricant testing assembly as set forth in claim 25 wherein first and second springs are mounted in said first and second bores to resiliently bias said first and second bushings into contact with said rotor.

27. A lubricant testing assembly as set forth in claim 26 wherein said rotor exhibits a spheroid shape.

28. A lubricant testing assembly as set forth in claim 8 wherein first and second springs are mounted in said first and second bores to resiliently bias first and second bushings into contact with said rotor.

29. A lubricant testing assembly as set forth in claim 21 including a pressurized media and means for coupling said media to bias said first and second bushings into contact with said rotor.

* * * * *